United States Patent [19]
Haber et al.

[11] Patent Number: 6,145,130
[45] Date of Patent: Nov. 14, 2000

[54] PUNCTURE INDICATOR FOR A SURGICAL GLOVE

[75] Inventors: Terry M. Haber, Beverly Hills, Calif.;
William H. Smedley, Kingman, Ariz.;
Clark B. Foster, Laguna Niguel, Calif.

[73] Assignee: Habley Medical Technology Corporation, San Diego, Calif.; a part interest

[21] Appl. No.: 09/411,277

[22] Filed: Oct. 4, 1999

[51] Int. Cl.⁷ .................................................. A41D 19/00
[52] U.S. Cl. ................................................ 2/161.7; 2/168
[58] Field of Search ................................. 2/16, 20, 159, 2/161.7, 160, 164, 167, 168, 169; 116/266, 270; 128/917; 428/69, 916

[56] References Cited

U.S. PATENT DOCUMENTS

| | | | |
|---|---|---|---|
| 4,881,277 | 11/1989 | Hogle | 2/169 |
| 5,224,221 | 7/1993 | Richardson et al. | 2/168 |
| 5,317,760 | 6/1994 | Best | 2/161.7 |
| 5,619,752 | 4/1997 | Haber et al. | 2/161.7 |
| 5,911,848 | 6/1999 | Haber et al. | 156/245 |

*Primary Examiner*—John J. Calvert
*Assistant Examiner*—Katherine Moran
*Attorney, Agent, or Firm*—Morland C. Fischer

[57] ABSTRACT

A visual indicator for a surgical glove by which to automatically and instantaneously alert a health care professional of the need to select a new glove should the structural integrity of the glove be compromised by a puncture or tear that could expose the wearer to a contagious and potentially life-threatening disease. The surgical glove includes outer and inner latex glove layers that have a space extending therebetween and a vacuum established within the space. The visual indicator includes a hollow, hemispherically shaped dome that is manufactured from an elastomeric material and is disposed entirely between the outer and inner glove layers so as to lie in continuous and uninterrupted fluid communication with the space. The visual indicator is adapted to be inflated from an as-packaged compressed condition to an expanded condition with air that is suctioned from the atmosphere via a puncture or tear through the outer glove layer and the space between the outer and inner glove layers. The visual indicator is maintained in continuous fluid communication with the space between the glove layers by either a series of vent slots formed through the hemispherically shaped dome or by a series of air holes formed through a rigid foundation plate assembly that extends across and closes the bottom of the hemispherically shaped dome.

20 Claims, 4 Drawing Sheets

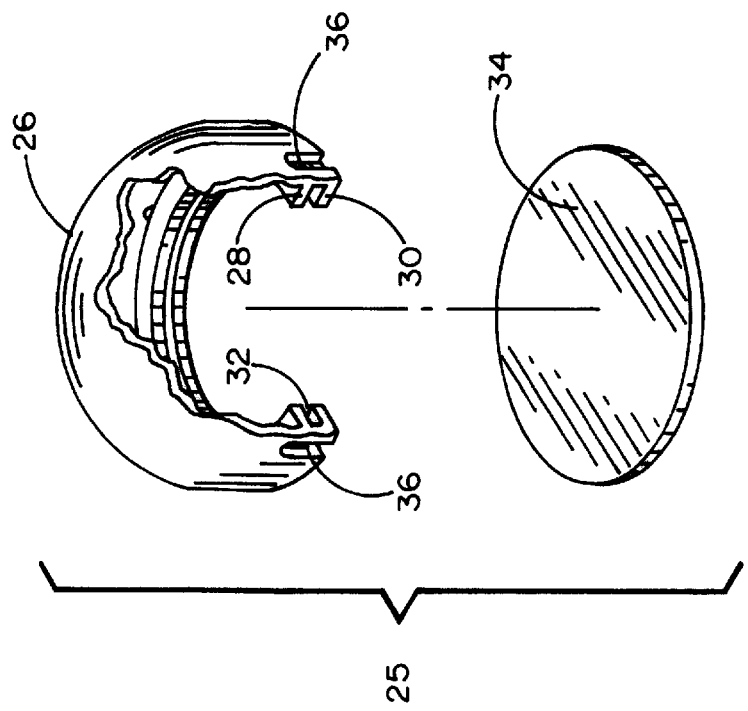
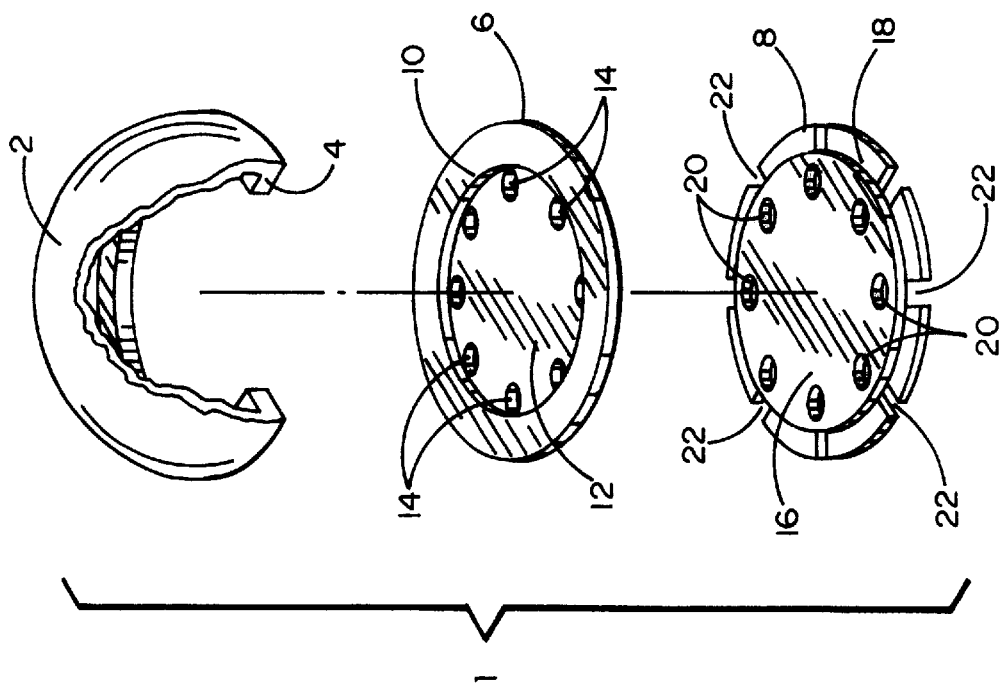

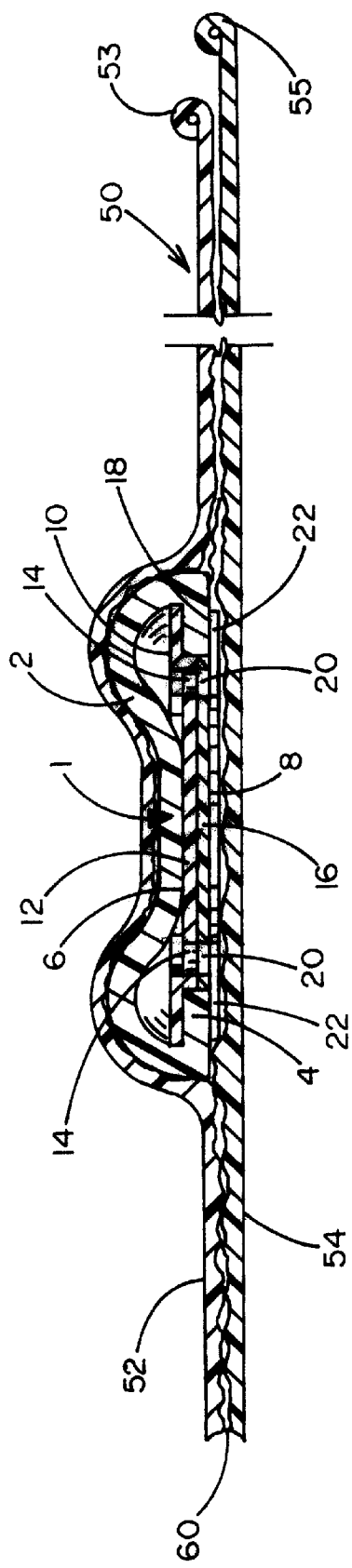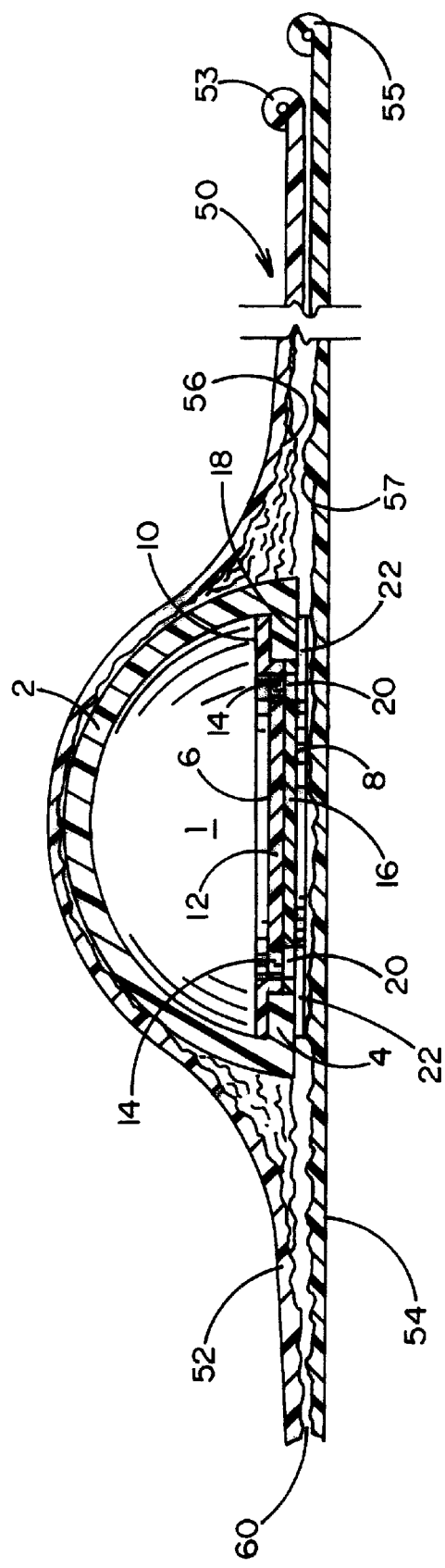

PUNCTURE INDICATOR FOR A SURGICAL GLOVE

BACKGROUND OF THE INVENTION

1. Field of the Invention

This invention relates to a surgical glove having an integral visual indicator by which to automatically and instantaneously alert a health care professional of the need to reglove should the structural integrity of the glove be compromised by a puncture or tear that could expose the wearer to a contagious and potentially life threatening disease.

2. Background Art

A rapidly growing problem facing surgeons and health care professionals who treat high risk patients is contracting nosocomial infection of hepatitis, AIDS and other contagious diseases through punctured, torn or otherwise structurally compromised surgical gloves. In some instances, the surgical glove may have a manufacturing defect (e.g. a pin hole). In other instances, where a sharp instrument such as a hypodermic cannula, scalpel, scissors and the like, is used in an operating theater, a surgeon may accidentally puncture his glove. In either instance, a penetration of the glove and the unsafe condition resulting therefrom often goes undetected until the health care professional removes his or her gloves at the end of the procedure and discovers a collection of blood inside the glove. Should the patient being treated have a contagious disease, the health care professional will be exposed to the possibility of contracting the disease and to the potentially life-threatening effects thereof. Some surgeons are under the misconception that accidental punctures may be avoided by simply double gloving. However, as a consequence of the very sharp instruments being used in an operating theater, double gloving will offer the surgeon little extra protection against an accidental puncture and the risks associated therewith.

U.S. Pat. No. 5,619,752 issued Apr. 15, 1997 describes a puncture evident surgical glove having an integral, non-obtrusive indicator bulb by which to accurately, instantaneously and visually alert a health care professional of the need to reglove as a consequence of a compromise in the structural integrity of the glove caused by a puncture or tear. The patented puncture evident glove includes outer and inner latex glove membranes that are spaced from one another to define an air flow path that is initially evacuated and sealed from the atmosphere. A flexible indicator bulb having a hollow body is sandwiched between the outer and inner membranes and adapted to expand to an inflated condition from an as-packaged compressed condition in response to the outer glove membrane being punctured or torn. Accordingly, the health care professional will be readily able to determine the status of his glove depending upon whether the indicator bulb is compressed or inflated.

While the aforementioned flexible indicator bulb is effective to provide a visual warning to health care professionals, the indicator bulb uses an exhaust tube and fluid valve connected between the bulb and the atmosphere. Moreover, the indicator bulb must first be pumped prior to the glove being worn so as to manually evacuate the air flow path between the outer and inner glove membranes and cause the bulb to assume the as-packaged compressed condition. What is still more, the precise location of the indicator bulb between the outer and inner glove membranes is important to assure immediate response to a puncture or tear through the glove.

In view of the foregoing, what would be desirable is a surgical glove, or the like, having improvements to the patented visual indicator bulb so as to eliminate the previously used exhaust tube and fluid valve and avoid a position-critical disposition of the bulb, whereby to reduce the part count and facilitate the manufacturing process. It would also be desirable that in the as-packaged state of the glove, the indicator bulb is initially evacuated so as to alert the health care professional to the patency of the glove prior to use. In this same regard, it would be desirable to avoid having to initially pump the bulb in order to manually evacuate the air flow path prior to the glove being worn.

SUMMARY OF THE INVENTION

In general terms, a relatively low cost and easy to manufacture visual indicator is disclosed for a puncture evident surgical glove, whereby to automatically and instantaneously alert a health care professional of the need to select a new glove or reglove should the structural integrity of the glove be compromised prior to or during use as a consequence of a puncture or tear that could expose the wearer to a contagious and potentially life threatening disease. The surgical glove includes outer and inner latex glove layers that are maintained in spaced alignment by means of opposing texturized surfaces having raised dimples that engage one another. The space between the outer and inner glove layers defines a fluid circuit (i.e. an air channel) that extends completely around the glove.

According to a first embodiment, the visual indicator includes a hollow, hemispherically shaped dome or bulb that is manufactured from an elastomeric (i.e. flexible) material that is adapted to inflate to an expanded condition from an as-packaged compressed condition to provide a visual indication that the structural integrity of a surgical glove has been compromised. Intermediate and lower foundation plates are arranged in opposing face-to-face alignment with one another to close the bottom of the indicator dome and prevent a gross distortion of the dome in the as-packaged compressed condition. A series of axial holes and radial slots are formed through the intermediate and lower foundation plates so that in the assembled configuration of the surgical glove, air passages are established by which the hollow interior of the indicator dome will remain in continuous and uninterrupted communication with the fluid channel between the outer and inner glove layers so that the visual indicator will immediately respond to a pressure change within the fluid channel.

According to a second embodiment, the visual indicator also includes a hollow, hemispherically shaped dome or bulb that is adapted to inflate to the expanded condition from the as-packed compressed condition in the event that the structural integrity of the glove is compromised. A single rigid foundation plate closes the bottom of the indicator dome and prevents a gross distortion of the dome in the as-packaged compressed condition. A series of vent slots are formed around the bottom of the indicator dome so that in the assembled surgical glove configuration, air passages are established by which the hollow interior of the indicator dome will remain in continuous and uninterrupted communication with the fluid channel between the outer and inner glove layers.

In operation, with the surgical glove in the as-packaged configuration for shipment to a health care facility, the indicator dome of the visual indicator is initially compressed and collapsed and the fluid circuit between the outer and inner layers of the surgical glove is evacuated such that a vacuum is established therearound. The indicator dome will remain in the as-packaged collapsed condition unless the structural integrity of the surgical glove is compromised as a consequence of a puncture or tear through at least the outer glove layer. In this case, the previously evacuated fluid circuit is placed in communication with the atmosphere, whereby air is suctioned to the interior of the hollow indicator dome via the fluid circuit around the glove and the air passages which link the fluid circuit to the dome. Accordingly, the hemispherically shaped indicator dome will automatically and instantaneously inflate to the expanded condition so as to provide a visual warning to a health care professional that the structurally compromised surgical glove should be discarded in favor of a new glove.

BRIEF DESCRIPTION OF THE DRAWINGS

FIG. 1 shows an exploded view of a puncture indicator according to a first embodiment of this invention for providing a visual indication that the structural integrity of a surgical glove has been compromised;

FIG. 2 shows the puncture indicator of FIG. 1 in the as-packaged evacuated (i.e. collapsed) condition;

FIG. 3 shows the puncture indicator of FIG. 1 in the inflated (i.e. expanded) condition when the structural integrity of the surgical glove has been compromised;

FIG. 4 shows an exploded view of a puncture indicator according to a second embodiment of this invention for providing a visual indication that the structural integrity of a surgical glove has been compromised;

DESCRIPTION OF THE PREFERRED EMBODIMENT

Figure 5:
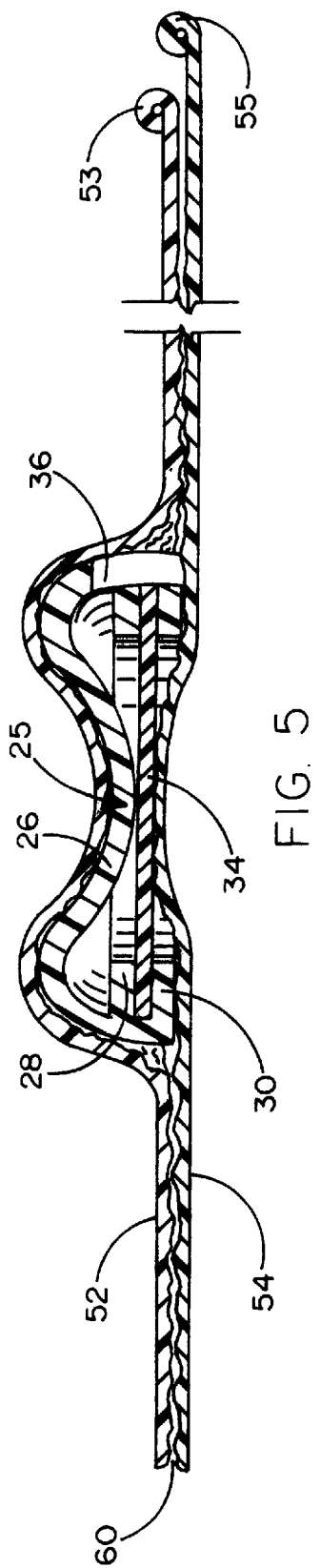
FIG. 5 shows the puncture indicator of FIG. 4 in the as-packaged evacuated (i.e. collapsed) condition.

The visual indicator 1 for a puncture evident latex surgical glove (designated 50 in FIG. 7) which forms a first embodiment of this invention is disclosed while referring initially to FIG. 1 of the drawings. The visual indicator 1 includes a hollow, hemispherically shaped indicator dome or bulb 2 that is manufactured from a high durometer elastomeric (i.e. flexible) material such as rubber, or the like. The dome 2 of indicator 1 is biased, under normal atmospheric pressure, to assume an inflated (i.e. expanded) condition as shown in FIG. 3. As will soon be explained, the indicator dome 2 is initially compressed in an evacuated (i.e. collapsed) condition as shown in FIG. 2 during the manufacture of the surgical glove 50.

However, because of a fluid (e.g. air) circuit around the glove 50 within which the visual indicator 1 is connected in the assembled glove configuration (best shown in FIGS. 2 and 3), the indicator dome 2 is adapted to automatically and instantaneously respond to a loss of vacuum and return from the evacuated condition to the inflated condition against the resistance offered by the latex material of the surgical glove 50. By virtue of the foregoing, the visual indicator 1 of the present invention will provide an immediate visual indication that the structural integrity of the glove 50 has been compromised as a consequence of a tear, abrasion or needle stick therethrough which could expose the wearer to a contagious and possible life threatening disease.

The hollow indicator dome 2 of visual indicator 1 is formed with an open bottom and a peripheral flange 4 extending therearound. The flange 4 projects inwardly of the indicator dome 2 for a purpose that will soon be described.

The visual indicator 1 also includes intermediate and lower foundation plates 6 and 8 that are coupled to the hollow indicator dome 2. Each of the intermediate and lower foundation plates 6 and 8 is manufactured from a metallic or rigid plastic material to prevent a gross distortion of the hemispheric indicator dome 2 when in the evacuated, collapsed condition (shown in FIG. 2) and maintain the hollow interior of indicator dome 2 in constant communication with the fluid circuit (designated 60 in FIGS. 2 and 3) around the surgical glove 50.

The intermediate foundation plate 6 has an annular rim 10 extending around a disk-like base 12. The base 12 of foundation plate 6 is recessed below the annular rim 10 thereof. A plurality of air holes 14 are arranged in a circular pattern and extend through the base 12 of plate 6. The lower foundation plate 8 also has a disk-like base 16 and an annular rim 18 extending therearound. The base 16 of lower foundation plate 8 lies above the rim 18. A plurality of air holes 20 are arranged in a circular pattern and extend through the base 16 of plate 8. A plurality of radial slots 22 are evenly spaced around the rim 18 of plate 8 so as to communicate with respective air holes 20 through the base 16.

In the assembled configuration shown in FIGS. 2 and 3 of the drawings, the rim 10 of the intermediate foundation plate 6 is seated upon the top of the peripheral flange 4 of the hemispheric indicator dome 2 so that the base 12 of plate 6 extends across the bottom of and closes the hollow interior of indicator dome 2. Similarly, the rim 18 of lower foundation plate 8 engages the bottom of peripheral flange 4. Therefore, the intermediate foundation plate 6 is held on one side of flange 4 between the lower foundation plate 8 on the other side of flange 4 and the indicator dome 2 such that the respective bases 12 and 16 of the intermediate and lower foundation plates 6 and 8 are arranged in opposing face-to-face alignment with one another. The bases 12 and 16 of intermediate and lower foundation plates 6 and 8 are preferably bonded together so as to maintain the hollow interior of indicator dome 2 in communication with the fluid circuit 60 around the surgical glove 50.

More particularly, and continuing to refer to the assembled configuration of FIGS. 2 and 3, with the bases 12 and 16 of the intermediate and lower foundation plates 6 and 8 arranged in opposite facing alignment, the respective through holes 14 and 20 thereof will be axially aligned with one another so as to communicate with the radial slots 22 in the rim 18 of lower foundation plate 8 to form a series of passageways to the hollow interior of indicator dome 2. In this same regard, the fluid circuit 60 around the surgical glove 50 remains in continuous and uninterrupted communication with the interior of indicator dome 2 via the aforementioned passageways through axially aligned through holes 14 and 20 and the radial slots 22 (best shown in FIG. 3) so that the visual indicator 1 will immediately respond to a pressure change within fluid circuit 60.

Figure 7:
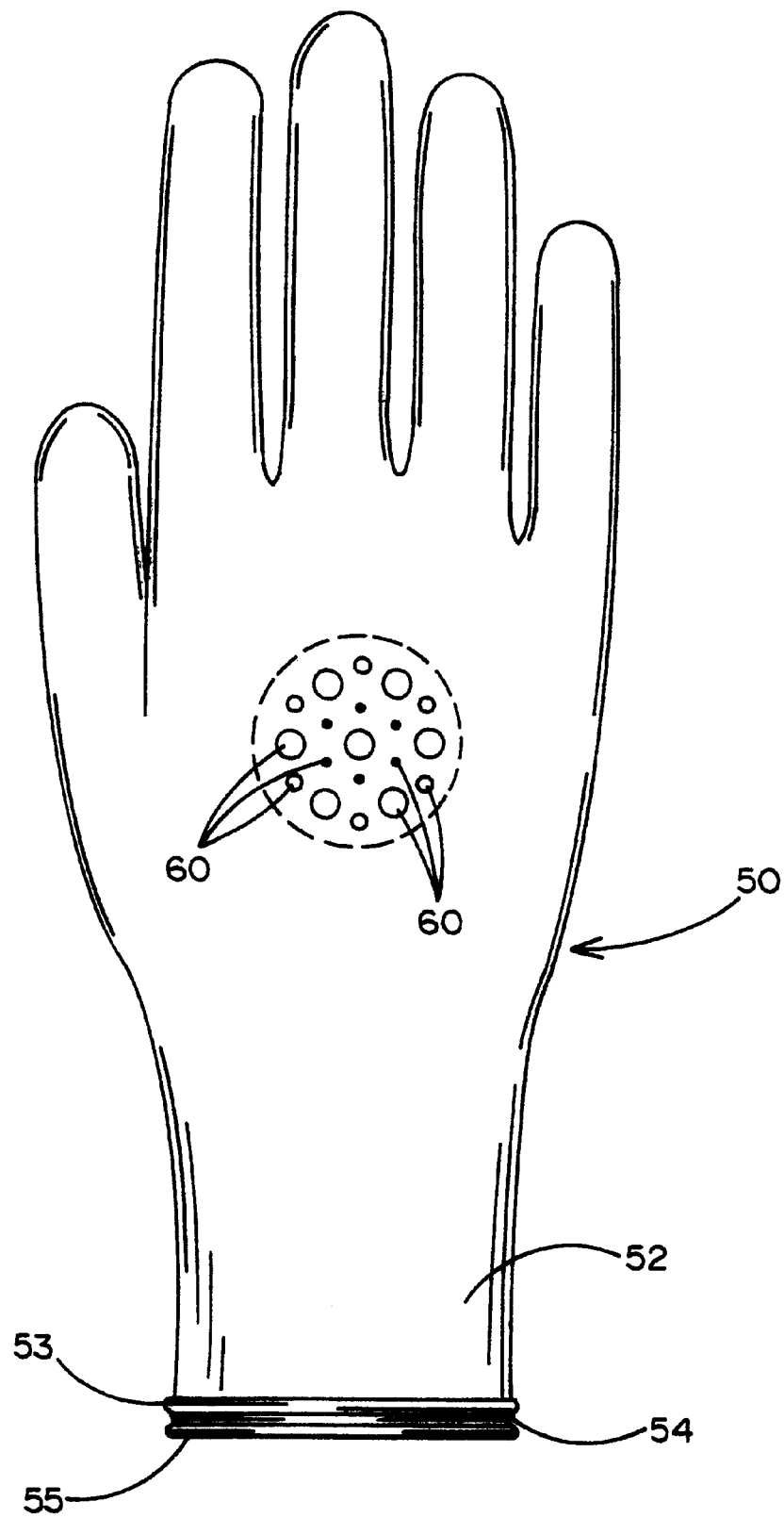
FIG. 7 shows a puncture evident surgical glove with one of the puncture indicators of FIGS. 1 or 4 integrally attached thereto.

The puncture evident surgical glove 50 shown in FIG. 7 is manufactured with oppositely facing outer and inner glove membranes or layers 52 and 54 of latex material. In other words, surgical glove 50 consists of a latex glove within a latex glove. The glove layers 52 and 54 are bonded to one another by means of a heat or adhesive seal at the respective cuff areas 53 and 55 thereof. Each of the outer and inner layers 52 and 54 of glove 50 has a texturized surface with a series of raised dimples 56 and 57, or the like, projecting outwardly therefrom. When the texturized outer and inner layers 52 and 54 of glove 50 are disposed one inside the other, the raised dimples 56 and 57 are positioned to oppose and engage one another, whereby to establish the aforementioned fluid circuit 60 (i.e. an air channel) by preventing the glove layers 52 and 54 from closing and sticking together. The fluid circuit 60 between the outer and inner glove layers 52 & 54 extends completely around the glove 50.

During manufacture of the surgical glove 50, the visual indicator 1 is disposed between the outer and inner glove layers 52 and 54. As an important advantage of this invention, the visual indicator 1 may be disposed at any convenient and inobtrusive location between the outer and inner glove layers 52 and 54 so as to be readily visible to the wearer. By way of example, the visual indicator 1 of the surgical glove 50 shown in FIG. 7 is located near the wrist area of the wearer so as to be immediately visible to and not interfere with the services being provided by the wearer, such as a heath care professional (e.g. a doctor or nurse), who by not wearing glove 50 could come into contact with the bodily fluids of his or her patient and risk the possibility of contracting a possibly contagious disease.

What is even more, the visual indicator 1 is permitted to float during manufacture of the puncture evident surgical glove 50. That is to say, the location of visible indicator 1 is not limited to any fixed position between the outer and inner latex glove layers 52 and 54 so long as the indicator lies in communication with the fluid circuit 60 that extends around the glove 50. Because of the ability of the visible indicator 1 to float prior to the outer and inner glove layers 52 and 54 being sealed together at cuff areas 53 and 55, the process for manufacturing the surgical glove 50 is made easier while the manufacturing costs can be correspondingly minimized.

The operation of the visual indicator 1 located between the outer and inner latex glove layers 52 and 54 of surgical glove 50 is now disclosed while continuing to refer to FIGS. 2 and 3 of the drawings. Turning first to FIG. 2, the visual indicator 1 is shown as-packaged where the hemispherically shaped indicator dome 2 is compressed to the collapsed condition during which the surgical glove 50 is shipped to a health care facility. In this case, all of the air is initially withdrawn from the fluid circuit 60 between the outer and inner glove layers 52 and 54 so as to establish a vacuum therewithin. Similarly, the hollow interior of indicator dome 2 and the passageway through the respective axially aligned through holes 14 and 20 and radial slots 22 of intermediate and lower foundation plates 6 and 8 which link indicator dome 2 to fluid circuit 60 are also evacuated.

Turning now to FIG. 3, the visual indicator 1 will remain in the as-packaged collapsed condition of FIG. 2 so long as the structural integrity of the surgical glove 50 is not compromised. However, should the glove be punctured or torn as a consequence of a needle stick, a scalpel cut, an abrasion, a manufacturing defect, or the like, prior to or while the glove is being worn, the indicator 1 will immediately respond to warn the health care professional of the need to reglove and/or select an altogether different glove.

That is, a puncture or tear anywhere through the outer layer 52 of glove 50 will place the previously evacuated fluid circuit 60 between glove layers 52 and 54 in communication with the atmosphere. In this case, air will be suctioned from the atmosphere to the interior of the indicator dome 2 via the fluid circuit 60 around the glove 50, the radial slots 22, and the axially aligned through holes 14 and 20 of foundation plates 6 and 8. Accordingly, the hemispherically shaped indicator dome 2 will automatically and instantaneously inflate to the expanded condition. The health care professional will then be able to use his tactile and/or visual senses to feel and/or see that the visual indicator 1 has been inflated to the expanded condition of FIG. 3 so as to have an accurate and immediate indication that the structural integrity of the surgical glove 50 has been compromised such that glove 50 should be discarded in favor of a new glove.

Figure 6:
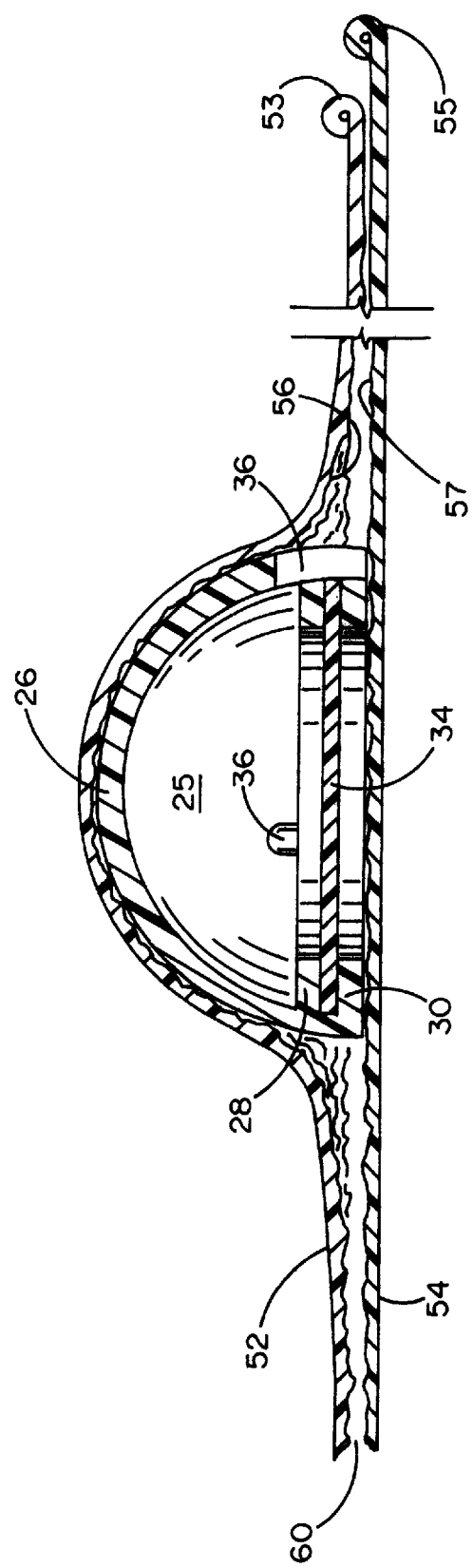
FIG. 6 shows the puncture indicator of FIG. 4 in the inflated (i.e. expanded) condition when the structural integrity of the surgical glove had been compromised.

Referring now to FIG. 4 of the drawings, there is shown a visual indicator 25 which forms an alternate embodiment of this invention. Similar to the visual indicator 1 of FIGS. 1–3, the visual indicator 25 of FIG. 4 includes a hollow, hemispherically shaped indicator dome or bulb 26 that is manufactured from an elastomeric (i.e. flexible) material and is adapted to expand to an inflated condition as shown in FIG. 6 from an as-packaged compressed or evacuated condition as shown in FIG. 5 when the structural integrity of the surgical glove has been compromised. Upper and lower peripheral flanges 28 and 30 extend around the open bottom of indicator dome 26 so as to form a channel 32 therebetween. A disk-like foundation plate 34 is manufactured from metal or rigid plastic and located within the channel 32 between the upper and lower flanges 28 and 30 so as to close the open bottom of indicator dome 2.

The single foundation plate 34 of the visual indicator 25 of FIG. 4 replaces the upper and lower foundation plates 6 and 8 of the visual indicator 1 of FIG. 1. Like the foundation plates 6 and 8 of visual indicator 1, the foundation plate 34 prevents a gross distortion of the hemispherically shaped indicator dome 26 when in the evacuated, collapsed condition and maintains the hollow interior of indicator dome 26 in constant communication with the previously described fluid circuit 60 that extends around the surgical glove 50 of FIG. 7 between the outer and inner latex glove layers 52 and 54. However, in substitution of the fluid passages formed by the through holes 14 and 20 and the radial slots 22 in the foundation plates 6 and 8 of indicator 1, vent slots 36 are formed in and spaced around the bottom of the indicator dome 26 of visual indicator 25. The vent slots 36 function to hold the hollow interior of dome 26 in continuous and uninterrupted communication with the fluid circuit 60 to enhance the responsiveness of the visual indicator 25 to a pressure change within fluid circuit 60.

The operation of the visual indicator 25 of FIG. 4 is identical to the operation of the visual indicator 1 of FIG. 1. Therefore, only a brief description of the operation of visual indicator 25 will be provided while referring to FIGS. 5 and 6 of the drawings. FIG. 5 shows the visual indicator 25 as-packaged where the hemispherically shaped indicator dome 26 is compressed to the collapsed condition during which the surgical glove 50 of FIG. 7 is shipped to a health care facility. In this same regard, all of the air is initially withdrawn from the indicator dome 26 and the fluid circuit 60 between the outer and inner glove layers 52 and 54 so that a vacuum is established therewithin. The visual indicator 26 will remain in the as-packaged, collapsed condition until the structural integrity of glove 50 is compromised before or during use.

FIG. 6 shows the visual indicator 25 when a puncture or tear is made through the outer layer 52 of glove 50, whereby the previously evacuated fluid circuit 60 between glove layers 52 and 54 is now placed in communication with the atmosphere. Thus, air is suctioned from the atmosphere to the interior of the indicator dome 26 via the fluid circuit 60 around the glove 50 and the vent slots 36 in dome 26. Accordingly, the hemispherically shaped indicator dome 26 will automatically and instantaneously inflate to the expanded condition to immediately provide a visual and/or tactile warning to the health care worker that the structural integrity of the surgical glove 50 had been compromised such that a new glove should be used in its place.

To enable the health care professional to quickly and easily identify the visual indicators 1 and 25 in the inflated, expanded condition of FIGS. 3 and 6, a set of indicia 60 (e.g. dots, circles and other geometric patterns) may be printed on the outer layer 52 of glove 50 (best shown in FIG. 7) above the location of the indicator. With the visual indicator 1 or 25 inflated, the printed indicia 60 will be prominently displayed to alert the wearer of the need to reglove.

It will be apparent that while a preferred embodiment of the invention has been shown and described, various modifications and changes may be made without departing from the true spirit and scope thereof. For example, while the visual puncture indicators 1 and 25 have been shown and described for warning that the structural integrity of a surgical glove has been compromised, it is to be expressly understood that the teachings of this invention are also applicable to indicating punctures, tears, abrasions, wounds, etc. in packages, the contents of which are to be isolated from the atmosphere. Thus, the package surrounding the contents would include the aforementioned outer and inner layers spaced from one another to establish a fluid (i.e. air) circuit with the visual indicator 1 or 25 disposed between such outer and inner layers so as to lie in communication with the fluid circuit. Should the outer layer of the package be prematurely opened (e.g. punctured or torn), the visual indicator will respond by providing an accurate and instantaneous warning that the package must be repaired or replaced to preserve the contents located therewithin.

Having thus set forth a preferred embodiment of this invention, what is claimed is:

1. For a puncture evident surgical glove having outer and inner glove layers that are separated from one another by a space and a vacuum established within said space, a visual indicator by which to provide an indication that the structural integrity of the surgical glove has been compromised as a consequence of a puncture or tear through at least the outer glove layer, said visual indicator comprising:
    a hollow flexible indicator body having a closed top and an open bottom, at least one rigid plate fixedly connected to and extending across the open bottom of said indicator body to close said open bottom and prevent a gross distortion of said flexible indicator body when said indicator body is compressed, and at least one air passageway through which said indicator body communicates with the space between the outer and inner glove layers, said indicator body being compressed to an air evacuated condition when the structural integrity of the surgical glove is not compromised and the vacuum is established within the space, and said indicator body being inflated with air from the atmosphere to an expanded condition via said air passageway in the event that the structural integrity of the surgical glove is compromised and the space between the outer and inner glove layers is filled with air suctioned from the atmosphere.

2. The visual indicator recited in claim 1, wherein said at least one air passageway through which said hollow flexible indicator body communicates with the space between the outer and inner glove layers is formed by at least one vent slot formed through said indicator body.

3. The visual indicator recited in claim 1, wherein said hollow flexible indicator body has a pair of flanges extending around the interior thereof such that a gap is established between said pair of flanges, said at least one rigid plate being received within said gap so as to close said open bottom and prevent a gross distortion of said indicator body when said indicator body is compressed to the air evacuated condition.

4. The visual indicator recited in claim 1, wherein said hollow flexible indicator body is a dome having a hemispherical shape when said indicator body is inflated to the expanded condition and the space between the glove layers is filled with air suctioned from the atmosphere.

5. The visual indicator recited in claim 1, wherein said at least one air passageway through which said hollow flexible indicator body communicates with the space between the outer and inner glove layers if formed by at least one hole through said at least one rigid plate.

6. The visual indicator recited in claim 1, wherein said hollow flexible indicator body has a flange extending around the interior thereof, said at least one rigid plate being seated upon and secured to said flange so as to close said open bottom and prevent a gross distortion of said indicator body when said indicator body is compressed to the air evacuated condition.

7. The visual indicator recited in claim 1, wherein said hollow flexible indicator body is located entirely between the outer and inner glove layers.

8. The visual indicator recited in claim 1, wherein said hollow flexible indicator body is manufactured from an elastomeric material.

9. The visual indicator recited in claim 1, including indicia printed on the outer glove layer and responsive to the inflation of said hollow flexible indicator body to said expanded condition to provide a further indication that the structural integrity of the surgical glove has been compromised.

10. In combination:
    an enclosure surrounding an article to be maintained in fluid isolation from the atmosphere, said enclosure having outer and inner layers that are separated from one another by a space and a vacuum established within said space between said outer and inner layers; and
    a visual indicator to indicate when the structural integrity of the enclosure has been compromised as a consequence of a puncture or tear through at least the outer layer of said enclosure, said visual indicator including a hollow flexible indicator body located between said outer and inner layers and lying in fluid communication with the space between said layers, said indicator body having at least one opening formed therein such that the hollow interior of said indicator body lies in continuous and uninterrupted fluid communication with the space between the outer and inner layers of said enclosure said indicator body being compressed to an air evacuated condition when the structural integrity of the enclosure is not compromised and the vacuum is established within the space between said outer and inner layers, and said body being inflated with air from the atmosphere to an expanded condition via said at least one opening and said space between said layers in the event that the structural integrity of said enclosure is compromised and said space is filled with air suctioned from the atmosphere.

11. The combination recited in claim 10, wherein said enclosure is a surgical glove and said outer and inner layers are first and second latex glove members lying one above the other such that said space is formed therebetween, and the article to be maintained in fluid isolation from the atmosphere is a human hand.

12. The combination recited in claim 10, wherein said hollow flexible indicator body has a closed top and a closed bottom, said at least one opening extending through said closed bottom.

13. The combination recited in claim 12, wherein the closed bottom of said hollow flexible indicator body is a rigid plate lying below said closed top to prevent a gross distortion of said indicator body in the air evacuated condition thereof.

14. The combination recited in claim 13, wherein said hollow flexible indicator body has a pair of parallel aligned flanges extending around the interior thereof such that a gap is established between said pair of flanges, said rigid plate being received within said gap so as to establish the closed bottom of said indicator body.

15. The combination recited in claim 13, wherein said hollow flexible indicator body has a flange extending around the interior thereof, said rigid plate being seated upon and secured to said flange so as to establish the closed bottom of said indicator body.

16. The combination recited in claim 10, wherein said hollow flexible indicator body is located entirely between the outer and inner layers of said enclosure.

17. The combination recited in claim 10, wherein said hollow flexible indicator body is manufactured from an elastomeric material.

18. The combination recited in claim 10, including indicia printed on the outer layer of said enclosure and responsive to the inflation of said hollow flexible indicator body to said expanded condition to provide a further indication that the structural integrity of the enclosure has been compromised.

19. The combination recited in claim 10, wherein said hollow flexible indicator body includes a dome having a hemispherical shape when said indicator body is inflated to the expanded condition and the space between the outer and inner layers of said enclosure is filled with air from the atmosphere.

20. The combination recited in claim 19, wherein said at least one opening formed in said hollow flexible indicator body is a vent slot formed through said dome.

* * * * *